United States Patent
Tamerlani et al.

(10) Patent No.: US 9,034,844 B2
(45) Date of Patent: May 19, 2015

(54) 6'-SIALYLLACTOSE SALTS AND PROCESS FOR THEIR SYNTHESIS AND FOR THE SYNTHESIS OF OTHER ALPHA-SIALYLOLIGOSACCHARIDES

(75) Inventors: Giancarlo Tamerlani, Castel di Casio (IT); Ilaria Lombardi, Montecatini (IT); Debora Bartalucci, Vinci (IT); Andrea Danesi, Pistoia (IT); Liana Salsini, Seravezza (IT); Marco Manoni, Vinci (IT); Giovanni Cipolletti, Milan (IT)

(73) Assignee: INALCO S.P.A., Milano (IT)

( * ) Notice: Subject to any disclaimer, the term of this patent is extended or adjusted under 35 U.S.C. 154(b) by 290 days.

(21) Appl. No.: 13/260,221

(22) PCT Filed: Apr. 6, 2010

(86) PCT No.: PCT/IB2010/051470
§ 371 (c)(1),
(2), (4) Date: Sep. 23, 2011

(87) PCT Pub. No.: WO2010/116317
PCT Pub. Date: Oct. 14, 2010

(65) Prior Publication Data
US 2012/0071441 A1 Mar. 22, 2012

(30) Foreign Application Priority Data
Apr. 6, 2009 (IT) .................. FI2009A0071

(51) Int. Cl.
*C07H 13/04* (2006.01)
*C07H 15/04* (2006.01)
*C07H 23/00* (2006.01)
*C07H 13/06* (2006.01)

(52) U.S. Cl.
CPC ............ *C07H 13/06* (2013.01); *A23G 2200/06* (2013.01); *C07H 13/04* (2013.01); *C07H 23/00* (2013.01); *C07H 15/04* (2013.01)

(58) Field of Classification Search
None
See application file for complete search history.

(56) References Cited

FOREIGN PATENT DOCUMENTS

| WO | 92/11017 | 7/1992 |
|---|---|---|
| WO | 94/03184 | 2/1994 |
| WO | WO94/03184 | * 2/1994 |
| WO | 2007/090894 | 8/2007 |

OTHER PUBLICATIONS

Rencurosi et al., Carbohydrate Research, 377, 2002, 473-483.*
Du, Y., et al., Stereospecific synthesis of α-C-glycosyl derivates ("α-C-glyosides") of N-acetylneuraminic acid by samarium-mediated reductive desulfonylation of a glycosyl phenylsulfone, Carb. Research 1998: 308: 161-164.
Schmidt, R., et al., Efficient sialylation with phosphite as leaving group, Tetrahedron Letters 1992, 33: 6123-6126.
Wong, C., et al., β-Sialyl phosphite and phosphoramidte: Synthesis and application to the chemoenzymatic synthesis of CMP-Sialic acid and sialyl oligosaccharides, JACS 1992, 114: 8748-8750.
Ito, Y., et al., Highly stereoselective glycosylation of N-acetylneuraminic acid aided by a phenylthio substituent as a stereocontrolling auxiliary, Tetrahedron Letters 1988, 29: 3987-3990.
Kononov, L., et al., Synthesis of a polymer-supported sialic acid glycosyl donor, Tetrahedron Letters 1997, 38: 1599-1602.
Kuhn, R., et al., Synthese anomerer Sialinsaure-methylketoside, Chem. Berichte 1966, 99: 611-617 (English translation of the abstract only).
Marra, A., et al., Stereoselective synthesis of 2-thioglycosides, Carb. Research 1989, 187: 35-42.
Marra, A., et al., Acetylation of N-acetylneuramunic acid and its methyl ester, Carb. Research 1989, 190: 317-322.
Byramova et al., A Simple Procedure for the Synthesis of the Methyl and Benzyl Glycosides of Neu5Ac and 4-epi-Neu5Ac. Conversion of the Benzyl and Methyl Glycosides of Neu5Ac into N-trifluoroacetylneuraminic acid Benzyl Glycosides, Carb. Res. 1992, 237: 161-175.
Dorland et al., 360-MHz H Nuclear-magnetic-resonance Spectroscopy of Sialyl-Oligosaccharides from Patients with Sialidosis (Mucolipidosis I and II), Eur. J. Biochem. 1978, 87: 323-329.
Kamerling et al., Structural Studies of 4-o-acetyl-α-n-acetylneuraminyl-(2→3)-lactose, the main oligosaccharide in echidna milk, Carb. Res. 1982, 100: 331-340.
Ichikawa et al., Enzyme-Catalyzed Oligosaccharide Synthesis, Anal. Biochem. 1992, 202: 215-238.
Sabesan et al., Combined Chemical and Enzymatic Synthesis of Sialyloligosacharides and Characterization by 500-MHz $^1$H and $^{13}$C NMR Spectroscopy, J. Am. Chem. Soc. 1986, 108: 2068-2080.
Hindsgaul et al., Evaluation of Deoxygenated Oligosaccharide Acceptor Analogs as Specific Inhibitors of Glycosyltransferases, J. Biol. Chem. 1991, 177: 17858-17862.
Gross et al., Enzymatic introduction of a fluorescent sialic acid into oligosaccharide chains of glycoproteins, Eur. J. Biochem. 1988, 177: 583-589.
Beyer et al., Glycosyltransferases and their use in Assessing Oligosaccharide Structure and Structure-Function Relationships, Adv. Enzymol. 1981, 52: 23-175.
Weinstein et al., Sialyation of Glycoprotein Oligosaccharides N-linked to Asparagine, J. Biol. Chem. 1982, 257: 13845-13853.
Koenigs et al., Ueber einige Derivate des traubenzuckers and der Galactose, Chem. Ber. 1901, 34: 957-963, 978-981 (English translation of the abstract only).

(Continued)

*Primary Examiner* — Traviss C McIntosh, III
(74) *Attorney, Agent, or Firm* — Steinfl & Bruno, LLP

(57) ABSTRACT

The present invention relates to a process of synthesis of α-sialyl oligosaccharides and in particular of 6'-sialyllactose and its salts comprising a step of coupling by Koenigs-Knorr reaction under conditions that allow its use on an industrial scale.

7 Claims, No Drawings

(56) References Cited

OTHER PUBLICATIONS

Helferich et al., Synthese einiger Disaccaride, J. Chem. Ber. 1962, 95: 2604-2611 (English translation of the abstract only).

Paulsen et al., Synthesis of Trisaccharide Moieties from N-Acetylneuraminic Acid and N-Acetyllactosamine, Angew. Chem. Int. Ed. Engl. 1982, 927-928.

Ress, D., et al., Sialic Acid Donors: Chemical Synthesis and Glycosylation, Current Organic Synthesis 2004, 1: 31-46.

PCT International Search Report for PCT/EP2010/051470 filed on Apr. 6, 2010 in the name of INALCO S.P.A.

PCT Written Opinion for PCT/EP2010/051470 filed on Apr. 6, 2010 in the name of INALCO S.P.A.

Italian Search Report for Italian Application FI2009A000071 filed on Apr. 6, 2009 in the name of INALCO S.P.A.

Italian Written Opinion for Italian Application FI2009A000071 filed on Apr. 6, 2009 in the name of INALCO S.P.A. (Italian and English).

Rencurosi, A., et al., Human milk oligosaccharides: an enzymatic protection step simplifies the synthesis of 3'- and 6'- 0-sialyllactose and their analogues, Carbohydrate Research 2002, 337: 473-483.

Muller, et al., Occurrence and Some Properties of Neuraminidases in Haemophilijs A Vium and Haemophilus Paragallinarum, Veterinary Microbiology 1978, 2: 303-312.

Pazynina, G., et al., Simple stereoselective synthesis of α2-6 sialooligosaccharides, Terta. Letters 2002, 8011-8013.

* cited by examiner

6'-SIALYLLACTOSE SALTS AND PROCESS FOR THEIR SYNTHESIS AND FOR THE SYNTHESIS OF OTHER ALPHA-SIALYLOLIGOSACCHARIDES

CROSS REFERENCE TO RELATED APPLICATIONS

The present application is the US national stage of International Application PCT/IB2010/051470 filed on Apr. 6, 2010, which, in turn, claims priority to Italian Patent Application FI2009A000071 filed on Apr. 6, 2009.

FIELD OF INVENTION

The present invention relates to the field of salts of 6'-sialyllactose: the present invention also relates to the field of processes for the synthesis of α-sialyl-oligosaccharides and in particular to the field of processes for the synthesis of 6'-sialyllactose and its salts.

BACKGROUND

α-Sialyl-oligosaccharides of formula (I)

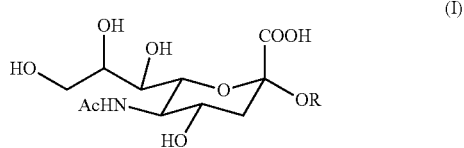

(I)

wherein R is a mono- di- or oligosaccharide residue with free hydroxyl groups are present in mammals and birds tissues and in predominant form of lipooligosaccharides, lipopolysaccharides or glycans of glycoproteins. They exist in a variety of glycosidic bonds, more typically α(2-3) and α(2-6) galactose (or lactose). The function of these sialosides varies greatly in animals according to the structural heterogeneity of the oligosaccharide portion. They are mediators of inter and intra-cells events in particular play an important role in the physiology and growth of many pathogen agents (D K Ress, et al., Current Organic Synthesis, 2004, 1, 31-46).

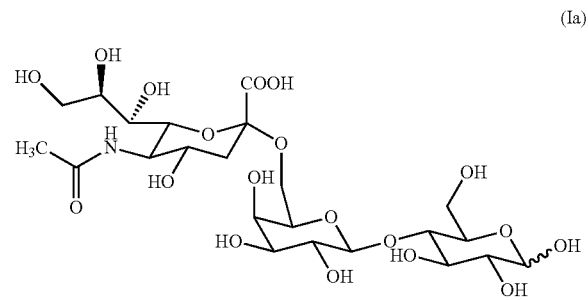 [SMILES: CC(=O)NC1C(O)CC(OCC2OC(OC3C(CO)OC(O)C(O)C3O)C(O)C(O)C2O)(C(=O)O)OC1[C@H](O)[C@H](O)CO]

(Ia)

One liter of human milk contains about 5-10 g of free oligosaccharides, this content is similar to the content of proteins and exceeds the lipid content. More than 130 different oligosaccharides were identified in human milk (Human Milk Oligosaccharides—HMO), formulations of artificial milk for babies derive from bovine milk and contain only trace amounts of these oligosaccharides that are specific of the human species. The fundamental building blocks of oligosaccharides of human milk are the 5 monosaccharides D-glucose (Glc), D-galactose (Gal), N-acetylglucosamine (GlcNAc), L-fucose (Fuc) and sialic acid (N-acetylneuraminic acid, Neu5Ac). The terminal reducing end can be formed by lactose (Galβ1-4Glc) or more repetitive units (up to 15 unit) of N-acetyllactosamine (Galβ1-3/4GlcNAc). Lactose or polylactosamine may be sialylated with α2-3 and/or α2-6 bonds. Examples of sialosides of human milk are: 3'-sialyl-3-fucosylactose (3'S3FL), 6'-sialyllactose (6'SL), 3'-sialyllactose (3'SL), 3'-sialyllattosamine (3'SLN), 6'-sialyllactosamine (6'SLN).

Among sialosides mainly present in mammalian tissues and in human milk the compound of formula (Ia) 6'-sialyllactose (N-acetylneuraminyl-lactose, α-NeuNAc-(2→6)-β-D-Gal-(1→4)-D-Glc or 6'-SL) is of particular importance because it is an important constituent of glycoproteins and glycolipids involved in various cell pathway events including cell recognition and immune response. The 6'-SL and their salts are interesting as supplements in food formulations for infants. As for the salts of the 6'-sialyllactose in literature only the sodium salt (CAS Number: 157574-76-0; FW: $C_{23}H_{38}NO_{19}Na$, 6'-sialyllactose sodium salt, 6'-N-Acetylneuraminyl-lactose sodium salt) and the ammonium salt are known. While the sodium salt is acceptable for food and pharmaceuticals, the ammonium salt is potentially toxic because of the ammonium ion. For this reason it is necessary to get 6'-SL in alternative salt forms to the known ones that may be acceptable for food and pharmaceuticals.

At the state of the art various strategies are known for synthesis of sialyl-oligosaccharides (including 6'SL) and all foresee a convergent approach in which the sialic activated fragment (donor) is regio- and stereo-selectively bound to the oligosaccharide portion (acceptor). For this key step of coupling in literature three different synthetic strategies are known which foresee an exclusively enzymatic approach, exclusively chemical or chemo-enzymatic.

As for the enzymatic pathways families of sialyltransferases and transialidases (enzymes that add the sialic acid to oligosaccharides in a strictly specific way) were used. Examples of this route of synthesis are reported in A. T. Beyer et al *Adv. Enzymol.*, 1981, 52, 23-175, in J. Weinstein et al. *J. Biol. Chem.*, 1982, 257, 13845-13853.

However several are the limitations in the use of these enzymes:
1) the limited availability of these enzymes
2) the need to synthesize the donor of activated substrate CMP-NeuAc, or PNP-NeuAc
3) the strict specificity of the sialyltransferases which reduces the flexibility in use for the synthesis of natural sialosides (Ichigawa Y. et al. *Analytical Biochem* 1992, 202, 215-238, S. Sabesan et al. *J. Am. Chem. Soc.*, 1986, 108, 2068-2080, O. Hindsgaul et al *J. Biol. Chem.*, 1991, 266, 17858-17862, H. J. Gross et al. *Eur. J. Biochem.* 1988, 177, 583-589).

As for the chemo-enzymatic pathways these include chemical synthesis of the acceptor and then enzymatic sialylation as in S. Sabesan et al., *J. Am. Chem. Soc.*, 1986, 108, 2068-2080.

Focusing exclusively on chemical ways it is emphasized that the formation of the glycosidic bond with sialic acid is a reaction rather difficult because it is hampered by the fact that the donor is electronically and sterically hindered by the geminal carboxyl group. Moreover, the lack of functional group on C-3 rules out its anchimeric assistance for controlling stereochemistry and leads to the formation of by-products through the reaction of elimination; finally the formation of the binding with α configuration is thermodynamically disadvantaged in relation to anomeric effect. In an attempt to remedy these defects in the state of the art various strategies have been developed for the preparation of suitably activated sialic donors and acceptor with adequately protected hydroxyl groups that are reacted through various glycosylation methods.

Regarding the sialic donor it is to be emphasized that the complicated molecular architecture imparts a substantial degree of difficulty in its synthesis, protection and activation. The multifunctional nature (3 secondary hydroxyl groups) as well as the tertiary anomeric center, complicate the work of synthetic chemist. Currently to the state of the art is well known that the sialic donor can be activated as 2-xanthate (A. Marra et al., *Carbohydr. Res.*, 1989, 187, 35), as 2-aryl sulphone (Y. Du et al, *Carbohydr. Res.*, 1998, 308, 161), as 2-phosphite (R R Schmidt et al., *Tetrahedron Lett.*, 1992, 33, 6123 or C H Wong et al., *J. Am. Chem. Soc.*, 1992, 114, 8748) or as 2-halo derivative. Among all these groups the halogen derivatives are preferable as the phosphite and the thio derivatives require toxic reagents for their synthesis and not easy to handle in the industry. Among the halogens the chloro derivative is preferred as it is stable and easy to synthesize, in fact the bromo derivative is unstable and tends easily to eliminate and lead to anomeric mixtures during glycosilation reactions. The fluoro derivative requires a more elaborate synthesis than the chloro derivative and tends to form β glycosidic bonds. The chloro derivative would be the easiest donor to make and use.

Regarding to the structure of the donor, other synthetic routes, still more complex than previous ones, require the inclusion on the C-3 of sialic acid of a functional group that gives anchimeric assistance in the glycosilation reaction to prevent competitive elimination in 2,3 position. For this reason groups such as phenylthio or phenylselenium have been introduced (Y. Ito et al., *Tetrahedron Lett.*, 1988, 29, 3987 or in L. O. Kononov et al., *Tetrahedron Lett.*, 1997, 38, 1599). These pathways thus require multiple steps to obtain the active donor for the glycosylation reaction generally starting from 2,3-dehydro NeuAc with yields that vary according to the obtained specificity and the ease of purification of the intermediates.

For this reason for the synthesis of sialyloligosaccharides of formula (I) and in particular the 6'SL it would be preferable to employ efficiently a simple sialylderivative as the 2-chloro-donor of formula (II)

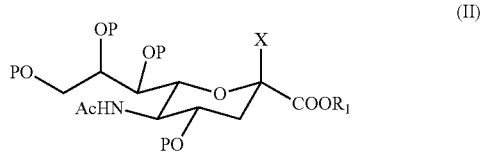

(II)

where P is a suitable protecting group, R1 is alkyl group and X is chlorine; (obtainable by methods reported in R. Kuhn et al., *Chem. Ber.*, 1966, 99, 611, A. Marra et al., *Carb. Res.*, 1989, 190, 317-322 and N F Byramova et al., *Carb. Res*, 1992, 237, 161-175) because it is also easily to synthesize on an industrial scale without the use of very toxic reactives, and it leads to the specific formation of α bonds in the glycosilation reactions. The use of this sialic donor, however, decreased significantly after its first applications and the state of the art addresses towards much more complex donors.

As for the acceptor activation for the synthesis of 6'SL, in the literature there are acceptors substituted with ether protective groups, for example benzyl groups whose removal, requiring an hydrogenation, is not easilymanageable (G. Pazynina et al. Tetrahedron Lett, 2002, 43, 8011-8013) and therefore difficult for industrial application.

α-glycosides of sialic acid were prepared by the Koenigs-Knorr reaction involving the use of Ag (I) as a promoter [Koenigs, W., Knorr, E. *Chem. Ber.*, 1901, 34, 957] or by using the Helferich modification that uses Hg (II) as promoter [Helferich, B.; Zirner, J. *Chem. Ber.*, 1962, 95, 2604]. The substrates chosen in these reactions are β-glycosyl-halides. Many variations of these classical methods are known which were designed to improve employment opportunities and yields. The main differences between these variations are related to the choice of counter anion of the metallic promoter. The most commonly used promoters are AgOTf, $Ag_2CO_3$, $HgX_2$ (X=halide), and $Hg(CN)_2$. In general it is known that Ag(I) promoters are more active and stereoselective (Pazynina G. et al. *Tetrahedron Lett*, 2002, 43, 8011-8013) but these should be used in large quantities (6-7 eq in relation to the acceptor) thus increasing the cost of synthesis (including the disposal of waste production), while Hg(II) promoters provide higher yields (H. Paulsen et al. Angew. Chem. Int. Ed. Engl, 1982, 927-928) but can present difficulties in handling due to their toxicity.

It is therefore evident the need for a process for the synthesis of compounds of formula (I) which is simple and economical, applicable on industrial scale, and hence allowing to overcome the technical problems above mentioned related to processes known in the literature.

SUMMARY OF THE INVENTION

The present invention solves the above problems by compounds of formula (Ib)

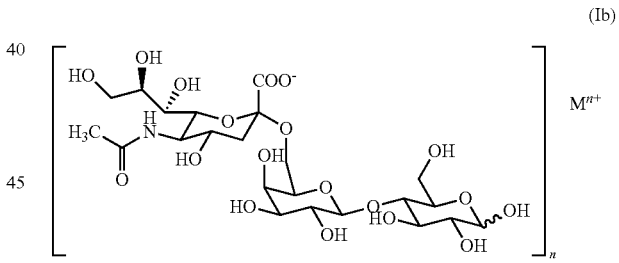

(Ib)

where $M^{n+}$ is chosen from the group consisting of $K^+$ $Ca^{2+}$ $Mg^{2+}$ $Sr^{2+}$ $Fe^{2+}$ $Al^{3+}$, Further subject-matter of the present invention is a process for the synthesis of α-sialyl-oligosaccharides (I) compounds of formula (I)

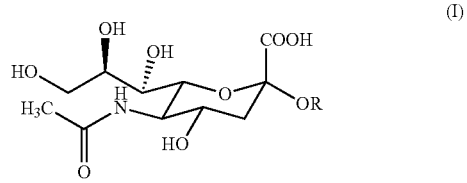

(I)

wherein R is a mono-, di- or oligossaccharide residue with free hydroxyl groups; said process comprising at least one step:

a) coupling by means of Koenigs-Knorr reaction of a sialic donor of formula (II)

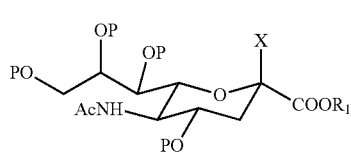

wherein P is a suitable protecting group, R1 is an alkyl group, and X is a halogen; with an acceptor of formula R'OH where R' is a mono-, di- or oligosaccharide residue suitably protected with protecting groups P' and containing zero, one or more free hydroxyl groups; these protecting groups P' may be the same or different from each other and from those present in the donor;

such Koenigs-Knorr reaction characterized by the fact that the metallic promoter based on Ag(I) is used in molar quantities between 0.5 and 2.0 eq respect to the moles of acceptor; to obtain an intermediate of formula (III)

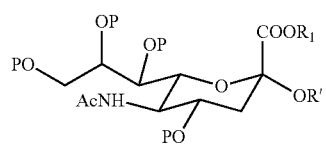

where P, R1 and R' are as defined above.

In particular, the process above mentioned provides a convenient route of synthesis for the 6'SL and then for its salts of formula (Ib) in which $M^{n+}$ is $Na^+$, $K^+$, $NH_4^+$, $Ca^{2+}$, $Mg^{2+}$, $Sr^{2+}$, $Fe^{2+}$, $Al^{3+}$.

Other advantages of the present invention are discussed later in the detailed description.

DETAILED DESCRIPTION

Subject matter of the present invention are compounds of formula (Ib)

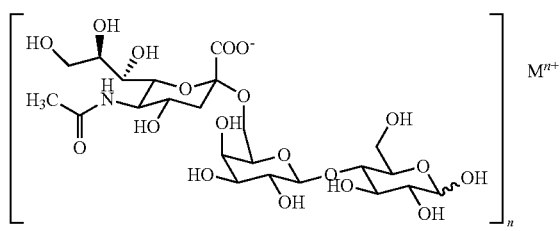

wherein $M^{n+}$ is chosen from the group consisting of $K^+$, $Ca^{2+}$, $Mg^{2+}$, $Sr^{2+}$, $Fe^{2+}$, $Al^{3+}$ where n=1, 2, 3 in correspondence to the oxidation state of M. Preferably $M^{n+}$ is $Ca^{2+}$, $Mg^{2+}$ o $K^+$.

Compounds of formula (Ib) are all alimentary and pharmaceutically acceptable and are useful as potential active ingredients or as food supplements (such as supplements in formulations of artificial milk for infants).

In particular 6'SL as:

calcium salt is potentially useful to promote bone growth;

potassium and magnesium salts are potentially useful in maintaining, promote or restore proper transport through biological membranes and the physiological difference of transmembrane potential;

iron salt is potentially useful for any pathological situations that require an integration of Fe;

The calcium salt in particular has better chemical-physical properties than the well-known sodium salt and its crystallization is easier. In fact during the crystallization phase, there is the formation of a crystalline solid, easy to be handled and thus easier to be managed even at industrial scale and its filtration has no problem because it is fast and allows an efficient washing of the solid.

In the case of sodium salt, instead, during the crystallization phase a rubbery solid is initially obtained, difficult to be stirred, which has to be grinded, and its filtration results slow and laborious. The stability of the two salts appears to be similar. Another positive aspect of the calcium salt is the fact that starting from a same matrix of 6'SL in acid form the calcium salt is the one obtained with higher purity: for example the same matrix of 6'SL has supplied a crystal of sodium salt at 87% HPLC purity and a crystal of calcium salt at 93% HPLC purity.

Both potassium and magnesium salts show chemical-physical characteristics similar to the sodium salt as well as their crystallization has a similar trend. Compounds of formula (Ib) above described can be prepared by 6'SL following known methods at state of the art for the preparation of salts from the corresponding carboxylic acids; for example they can be preferably prepared from a solution of 6'SL by adding a base containing $M^{n+}$ such as hydroxides, carbonates or bicarbonates (ie, KOH, $Ca(OH)_2$, $Mg(OH)_2$, etc., $K_2CO_3$, $CaCO_3$, $MgCO_3$ etc.; $KHCO_3$, etc.) until pH 8-10. After removal of the solvent the obtained salt are purified by crystallization from alcohols or mixtures of water/alcohol; preferably methanol, ethanol and their mixtures with water.

Optionally before the removal of the solvent it is possible to remove the excess of undissolved base by filtration, if present.

For another aspect the present invention relates to a process for the synthesis of α-sialyl-oligosaccharides of formula (I)

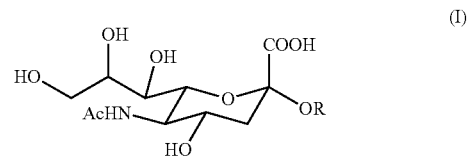

wherein R is a mono-, di- or oligosaccharide residue with free hydroxy groups, preferably R is selected between galactose, glucose, glucosamine, lactose, lactosamine, fucosillactose; more preferably R is selected between 6'-galactose, 3'-glucose, 3'-glucosamine, 6'-lactose, 3'-lactose, 6'-lactosamine 3'-lactosamine, 3'-3-fucosillactose;

such process involving at least one step:
a) coupling by Koenigs-Knorr reaction of a sialic donor of formula (II)

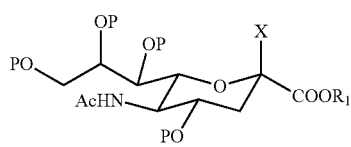

(II)

wherein:
P is a suitable protecting group;
R1 is an alkyl, preferably Me, Et, or Pr;
X is a halogen, preferably chlorine;
with a suitably protected acceptor of formula R'OH in which R' is a mono-, di- or oligosaccharide residue suitably protected with protecting groups P' and containing zero, one or more free hydroxyl groups: these protecting groups P' can be equal or different from each other and from those present in the donor; said Koenigs-Knorr reaction is characterized by the fact that the metallic promoter based on Ag (I) is used in molar quantities between 0.5 and 2.0 eq compared to moles of acceptor; to obtain an intermediate of formula (III)

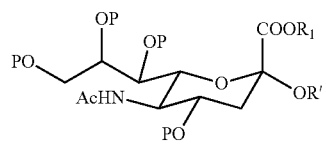

(III)

where P, R1 and R' are defined as above.
For a preferred aspect this process also includes after step (a), the following step:
b) removal of protective groups P, P' and R1 to obtain compounds of formula (I) as described above.
The removal of the protective group b) is performed according to methods known to the state of the art (T W Green and P G M WUTS. Green's Protective Groups in Organic Synthesis. Ed Wiley ed 4, 2006).
For a preferred aspect this metallic promoter is used in molar amount between 0.75 and 0.85 molar eq compared to moles of acceptor.
For a preferred aspect said metallic promoter is selected between Ag(I) salts such as AgOTf, $Ag_2CO_3$, and more preferably is $Ag_2CO_3$.
For a preferred aspect the coupling a) is conducted in aprotic polar solvent, preferably is conducted in dichloromethane.
For a preferred aspect said coupling a) is achieved by stirring the mixture at a temperature between 20 and 40° C. for a time between 5 and 10 days; preferably the mixture is stirred at 30° C. for 7 days.
For a preferred aspect P and P' are independently selected between benzyl and acyl, preferably P and P' are independently selected from acetyl, benzoyl or benzoyl mono- or di-substituted with alkoxy, halogen, nitro groups.
For a preferred aspect P and P' are acyls. For a more preferred aspect P and P' are equal and are acetyl. Where R is 6'-lactose in the process of the present invention with P=P'=Ac there is an additional distinction from known processes for the synthesis of 6'SL as in this case the acceptor used in the present invention do not show benzyl groups and consequently has the advantage of avoiding catalytic hydrogenation for the removal of protective groups.

For a preferred aspect this acceptor R'OH adequately protected has a free and reactive hydroxyl group at C-6 of the galactosidic moiety, in a particularly preferred aspect the acceptor is a lactose derivative of formula (IV):

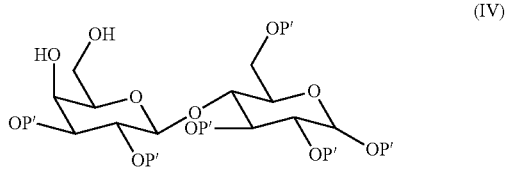

(IV)

where P' is a suitable protecting group; preferably P' is acyl, more preferably acetyl.
For a particularly preferred aspect therefore the present invention relates to the synthesis of 6'SL of formula (Ia) where R=6'-lactose by the process above described in which P and P' are Ac, X is chlorine and R1 is methyl; in this particular combination, the coupling reaction in which the acceptor is a compound of formula (IVa)

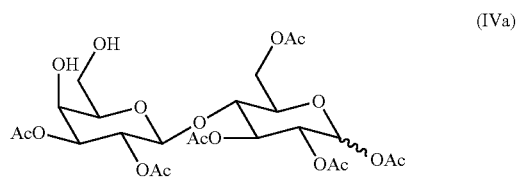 [SMILES: CC(=O)OCC1OC(OC(C)=O)C(OC(C)=O)C(OC(C)=O)C1OC1OC(CO)C(O)C(OC(C)=O)C1OC(C)=O]

(IVa)

provides the compound of formula (IIIa)

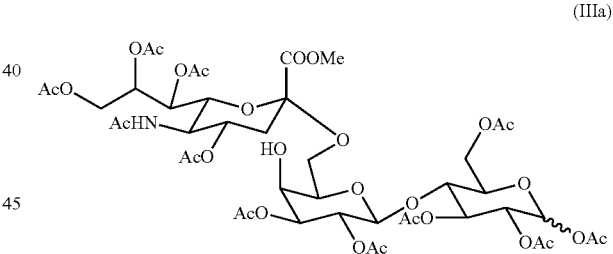

(IIIa)

that surprisingly can be used as it has been obtained from the crude mixture to the subsequent reaction of sequential deprotection of the hydroxyl groups and of the carboxyl function to the anomeric carbon of the sialic acid and production of the compound 6'SL formula (Ia). Preferably it has to proceed first to the removal of acetyl groups and then to the hydrolysis of methyl ester.
This sequential deprotection is carried out as known to the state of the art. Preferably the removal of the Ac groups is performed using a base such as sodium methoxide, sodium ethoxide or sodium hydroxide, more preferably sodium methoxide, using a primary alcohol as a solvent, like methanol or ethanol, most preferably methanol. Preferably the hydrolysis of methyl ester at anomeric carbon of the sialic acid is carried out in basic conditions with NaOH 1M.
Preferably when the methyl ester hydrolysis is completed, final acidification of the reaction mixture is performed by ion exchange resins, in particular a strong cationic resin and a weak anionic resin, to obtain an eluate containing 6'SL.

The sialic donor used in the process above described, in particular when X is chlorine and R' is lactose protected by formula (IV) with P=P'=Ac, is simple or easy to prepare and easy to use. This choice has revealed surprisingly adequate to solve the problems of known processes, despite the state of the art had directed towards much more complex donors.

The amount of promoter metal used in step a) is surprisingly reduced compared to the known state of the art, 0.5-2.0 eq versus 6-7 eq, and therefore reduces the cost of synthesis and the costs of disposing of waste production.

The product of coupling reaction is achieved surprisingly with enough purity to be used as it is in the subsequent reaction of deprotection to obtain the deprotected sialyl-oligosaccharides with good yields and purity. Furthermore it should be noted that the process for the coupling reaction of the present invention is stereoselective because the α isomer is the only one obtained.

The process of the present invention is therefore feasible on industrial scale.

The present invention also refers to a process for the synthesis of compounds of formula (Ib) in which $M^{n+}$ is $Na^+$, $K^+$, $NH_4^+$, $Ca^{2+}$, $Mg^{2+}$, $Sr^{2+}$, $Fe^{2+}$, $Al^{3+}$ such process including the preparation of 6'SL through the process above described; preferably the salts of formula (Ib) may be prepared directly by the eluate containing 6'SL, obtained after ion exchange resins treatment after hydrolysis of methyl ester, by addition of a base containing $M^{(n+)}$ such eg hydroxides, carbonates or bicarbonates (ie, KOH, $Ca(OH)_2$, $Mg(OH)_2$, etc., $K_2CO_3$, $CaCO_3$, $MgCO_3$ etc.; $KHCO_3$, etc.) until pH 8-10.

Compounds of formula (II) can be obtained by techniques known to the state of the art such as reported in (R. Kuhn et al., *Chem. Ber.*, 1966, 99, 611, A. Marra et al., *Carb. Res*, 1989, 190, 317-322 and N F Byramova et al., *Carb. Res*, 1992, 237, 161-175).

The synthesis of the suitably protected acceptor can be carried out following the knowledge of the man of the art, in particular the synthesis of the acceptor of formula (IIIa) where P is Ac was carried out according to methods known in agreement with the Scheme 1.

Schema 1

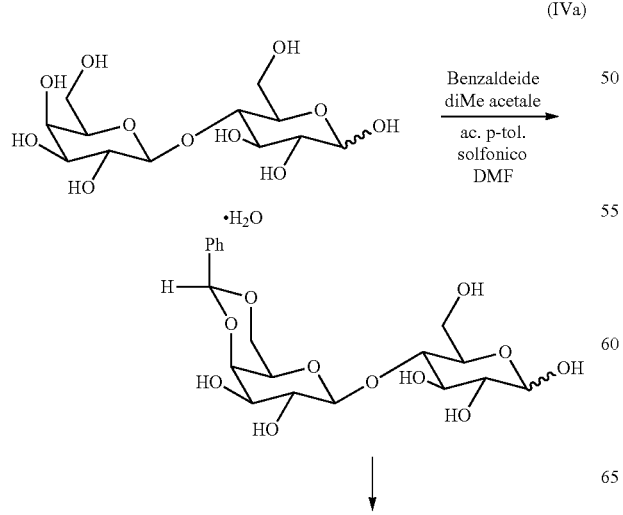

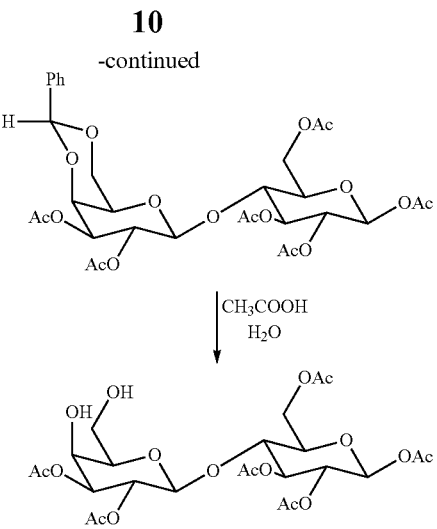

According to the invention alkoxy means, for example -OMe, -OEt, -OnPr, -OiPr, -OnBu, -OiBu, -OtBu.

According to the invention halogen means fluorine, chlorine, bromine, iodine. According to the invention alkyl is a linear alkyl chain or branched containing 1 to 6 atoms of carbon possibly substituted by one or more groups selected between halogen, hydroxy, alkoxy, nitro.

According to the invention aryl is benzene eventually replaced by one or more groups selected from halogen, alkoxy, nitro.

According to the invention acyl means a group —OCO-alkyl, or —OCO-aryl in which alkyl and aryl are defined as above.

According to the invention monosaccharide means a polyoxyaldeide (aldose) or a polyoxyketone (ketose) or a simple sugar of formula $(CH_2O)_n$, $C_nH_{2n}O_{n-1}$, $C_nH_{2n}O_{n-1}NH_2$ or $C_nH_{2n}O_{n-1}NHAc$ with n=3, 4, 5, 6.7; it means within the definition all the possible stereoisomers and all open or cyclic forms or intramolecular semi acetates and semiketales as an example the pyranosyl and furanosyl forms; for example, glyceraldehyde, allose, altrose, arabinose, eritrose, fucose, galactose, glucose, glucosamine, N-acetyl-glucosamine, idose, lixose, mannose, psychose, ribose, deoxyribose, sorbose, tagatose, treose, xylose and corresponding ketoses are included in the definition.

According to the invention disaccharide means a compound polyoxydrilated consisting of two monosaccharides linked through an acetalic or glycosidic both O-glycosidic or N-glycosidic bond; within the definition are included all of the possible stereoisomers and all forms of open or cyclic; for example lactose, lactosamine, N-acetyl-lactosamine, maltose, cellobiose, sucrose, threalose, turanose are included.

According to the invention oligosaccharide means a polymer formed of three to 6 monosaccharides joined together by glycosidic bonds to form linear saccharide chains or branched, for example raffinose, melezitose, maltotriose, acarbose, stachyose are included.

EXPERIMENTAL PART

Example 1

Preparation of di 4',6'-O-benzylidenlactose 200 g (0.555 mol) of lactose monohydrate were added under stirring to 1.4 l of N,N-dimethylformamide and then 209 ml (1.39 mol) of benzaldehyde dimethyl acetal and 5.28 g (0.028 mol) of p-toluenesulfonic acid monohydrate were added. The resulting suspension was heated at 55° C. and the temperature was maintained until TLC was successful (16-18 hours) (Pharmacopoeia). After cooling at room temperature 4.7 ml of triethylamine were added until pH 7-8. The mixture was concentrated to obtain 700 ml of solution, which is drained in 3 liters of hot acetone (50-55° C.), maintaining a vigorous stirring. The precipitation was completed by cooling the mixture to 0±5° C. The precipitate was filtered, washed with 0.7 liters of cold acetone and dried, obtaining 208 g of 4',6'-O-benzylidene lactose (mixture of α/β anomers) as white product (assay HPLC 66%, 0319 mol, yield: 57%).

By double crystallization, first by MeOH and then by MeOH/H$_2$O 4/1 v/v, an analytical sample enriched in a anomer was obtained, the NMR characterization is reported:

$^1$H NMR (DMSO d$_6$, 300 MHz): δ ppm 7.51-7.34 (5H, m, Ph); 6.36 (d, J$_{OH-1}$=4.8 Hz, 1H, C1-OH); 5.58 (s, 1H, PhCH); 5.28 (d, J=4.2 Hz, 1H, OH); 5.01 (d, d=5.7 Hz, OH); 4.92 (pseudo t, J$_{1-OH}$=J$_{1-2}$=4.0 Hz, 1H, H-1); 4.68 (d, J=6.9 Hz, 1H, OH); 4.45 (m, 2H, 2×OH); 4.37 (d, J$_{1'-2'}$=7.5 Hz, 1H, H-1'); 4.16-3.95 (m, 3H); 3.84-3.11 (m, 9H) (H-2, H-3, H-4, H-5, CH$_2$-6, H-2', H-3', H-4', H-5', CH$_2$-6').

$^{13}$C NMR (DMSO d$_6$, 75 MHz): δ ppm 138.5, 128.6, 127.9, 126.2 (Ph); 103.1 (C-1'); 99.8 (PhCH); 92.1 (C-1); 79.6, 75.8, 72.2, 71.6, 71.3, 69.9, 69.8, 68.5 (C2, C2', C3, C3', C4, C4', C5, C5'); 66.2 (C6'); 60.3 (C6).

Rf (pharmacopoeia, UV-vis and naftoresorcine)=0.7

Example 2

Preparation of 4',6'-O-p-methoxybenzylidenlactose 200 g (0.555 mol) of lactose monohydrate were added under stirring to 1.4 l of N,N-dimethylformamide and then 237 ml (1.39 mol) of p-methoxybenzaldehyde dimethyl acetal and 5.28 g (0.028 mol) of p-toluenesulfonic acid monohydrate were added. The resulting suspension was heated at 55° C. and the temperature was maintained until positive TLC resulted (16-18 hours) (Pharmacopoeia). After cooling at room temperature 5.0 ml of triethylamine were added until pH 7-8. The mixture was concentrated and the residue was crystallized in 3 liters of hot acetone (50-55° C.). The precipitation was completed by cooling the mixture at 0÷5° C. The precipitate was filtered, washed with 2×200 ml of cold acetone, obtaining 219 g of 4',6'-O-p-metossibenzyliden lactose (mixture of α/β anomers) as a pale yellow solid (assay HPLC 76%, 0361 mol, yield: 65%) Crystallization from hot acetone/H2O 4/1 v/v gave an analytical sample as a dip anomeric mixture (1/1 mol/mol), the NMR characterization is reported.

$^1$H NMR (DMSO d$_6$, 300 MHz): δ ppm 7.38 (d, J=8.7 Hz, 2H), 6.93 (d, J=8.7 Hz, 2H) (Ph); 6.70 (d, J$_{OH-1}$=6.6 Hz, 1H, C1-OH β); 6.36 (d, J$_{OH-1}$=4.1 Hz, 1H, C1-OH α); 5.52 (s, 1H, PhCH α+β); 5.27 (m, 1H, OH α+β); 5.04-4.95 (m, 1H, OH α+β); 4.92 (pseudo t, J=4.1 Hz, H-1α); 4.72-4.60 (m, 1H, OH α+β); 4.56-4.28 (m, H-1'α+β+H-1β+2×OH α+β); 4.12-3.92 (m, 3H); 3.76 (s, 3H, OMe); 3.80-3.11 (m, 9H); 2.98 (m, 1H β).

$^{13}$C NMR (DMSO d$_6$, 75 MHz): δ ppm 159.4, 130.9, 127.6, 113.2 (Ph); 103.0 (C-1' α+β); 99.7 (PhCH α+β); 96.7 (C-1β); 92.1 (C-1α); 79.6, 79.2, 75.7, 74.9, 74.8, 74.6, 72.2, 71.6, 71.3, 69.9, 69.8, 68.4 (C2, C2', C3, C3', C4, C4', C5, C5' α+β); 66.2 (C6' α+β); 60.4, 60.3 (C6α+β); 55.1 (OMe α+β).

Rf (pharmacopoeia, UV-vis and naftoresorcine)=0.8

Example 3

Preparation of 1,2,3,6,2',3'-hexa-O-acetyl-4',6'-O-benzyliden-β-D-lactose 100 g (0.153 moles from HPLC) of 4',6'-O-benzylidenlactose obtained according to example 1 and 256 ml (1.84 mol) of triethylamine were added to 600 ml of methyl ethyl ketone. The reaction mixture was heated at 60° C. and 174 ml (1.84 mol) of acetic anhydride were dropped maintaining the internal temperature below 70° C. The reaction mixture was stirred at 70° C. until TLC was successful (10-12 hours) (AcOEt). The solvent was evaporated and the residue dissolved in 270 ml of dichloromethane and 200 ml of water. NaOH 30% was added under stirring up to pH 9-9.5, then the layers were separated; the aqueous layer was extracted again with 75 ml of dichloromethane. The collected organic layers were washed with 200 ml of water, and then HCl solution 32% was added under stirring up to pH 1-1.5. The acid aqueous layer was extracted with 75 ml of dichloromethane. The collected organic layers were then washed with 370 ml of NaCl 20%, dried over anhydrous Na$_2$SO$_4$ and decolorized with charcoal and bentonite. The solvent was concentrated and the residue used as such in the next reaction. HPLC dosage gave 103 g (0.151 mol) of 1,2,3,6,2',3'-hexa-O-acetyl-4',6'-O-benzylidene lactose essentially as β anomer (α anomer <10 mol %) (yield: 99%). An analytical sample containing 9 mol % of α anomer was obtained by crystallization from hot MeOH; following is the NMR characterization (β anomer).

$^1$H NMR (CDCl$_3$, 300 MHz): δ ppm 7.54-7.34 (m, 5H, Ph); 5.68 (d, 8.4 Hz, 1H, H-1), 5.47 (pseudo s, 1H, CHPh); 5.32-5.21 (m, 2H, H-3+H-2'), 5.07 (dd, J$_{2-3}$=9.6 Hz e J$_{2-1}$=8.4 Hz, 1H, H-2), 4.87 (dd, J$_{3'-2'}$=10.4 Hz e J$_{3'-4'}$=3.8 Hz, 1H, H-3'), 4.54-4.43 (m, 2H, H-1'+H-6a), 4.38-4.25 (m, 2H, H-4'+H-6'a), 4.14 (dd, J$_{6b-6a}$=12.2 e J$_{6b-5}$=4.6 Hz, 1H, H-6b), 4.04 (d, J$_{6'b-6'a}$=12.3 Hz, 1H, H-6'b), 3.90-3.70 (m, 2H, H4+H5); 3.46 (pseudo s, 1H, H-5'), 2.14-2.00 (6×COCH$_3$).

$^{13}$C NMR (CDCl$_3$, 75 MHz): δ ppm 170.8, 170.4, 170.1, 169.7, 169.0, 168.9 (6×COCH$_3$); 137.5, 129.3, 128.3, 126.6 (Ph); 101.4 (CHPh); 101.1 (C-1'); 91.8 (C-1); 75.5, 73.8, 73.2, 72.4, 72.2, 70.5, 69.0, 68.5 (C-2, C-3, C-4, C-5, C-2', C-3', C-4', C-5'); 66.6 (C-6'); 61.8 (C-6), 20.9-20.7 (6×COCH$_3$).

Rf (AcOEt:hexan=1:1, UV-vis and H$_2$SO$_4$/MeOH)=0.3

Example 4

Preparation of 1,2,3,6,2',3'-hexa-O-acetyl-4',6'-O-p-methoxybenzyliden-β-D-lactose 100 g (HPLC dosage 0.165 mol) of 4',6'-O-p-methoxybenzylidenlactose obtained according to example 2 and 242 ml (1.74 mol) of triethylamine were added at 600 ml of methyl ethyl ketone. The suspension was heated at 60° C. and 164 ml (1.74 mol) of acetic anhydride were dropped maintaining the internal temperature below 70° C. The reaction mixture was stirred at 70° C. until positive TLC was successful (10-12 hours) (AcOEt:hexane=1:1). The solvent was evaporated and the residue dissolved in 270 ml of dichloromethane and 200 ml of water. NaOH 30% was added under stirring up to pH 9-9.5, then the layers were separated; the aqueous layer was extracted again with 75 ml of dichloromethane. The collected organic layers were washed with 200 ml of water, and then HCl solution 32% was added under stirring up to pH 1-1.5. The acid aqueous layer was extracted with 76 ml of dichloromethane. The collected organic layers were then washed with 400 ml of saturated NaHCO$_3$, with 400 ml of NaCl 20%, dried on anhydrous Na$_2$SO$_4$ and bleached with charcoal and bentonite. The solvent was concentrated and the residue used as such in next reaction, HPLC dosage gave 110 g (0.155 mol) of 1,2,3,6,2',3'-hexa-O-acetyl-4',6'-O-p-methoxybenzylidenlactose essentially as β anomer (yield: 94%). An analytical sample was obtained by crystallization from hot MeOH; following is the NMR characterization (β anomer).

$^1$H NMR (CDCl$_3$, 300 MHz): δ ppm 7.36 (d, J=8.7 Hz, 2H), 6.88 (d, J=8.7 Hz, 2H) (Ph); 5.66 (d, J$_{1-2}$=8.4 Hz, 1H, H-1); 5.40 (pseudo s, 1H, CHPh); 5.24 (pseudo t, J$_{3-2}$=J$_{3-4}$=9.6 Hz, 1H, H-3); 5.23 (dd, J$_{2'-3'}$=10.2 Hz e J$_{2'-1'}$=7.8 Hz, 1H, H-2'); 5.04 (dd, J$_{2-3}$=9.6 Hz e J$_{2-1}$=8.4 Hz, 1H, H-2): 4.84 (dd, J$_{3'-2'}$=10.2 Hz e J$_{3'-4'}$=3.6 Hz, 1H, H-3'), 4.46 (dd, J$_{6a-6b}$=12.0 Hz e J$_{6a-5}$=1.5 Hz, 1H, H-6a), 4.44 (d, J$_{1'-2'}$=7.8 Hz, 1H, H-1'); 4.28 (d, J$_{4'-3}$=3.6 Hz, 1H, H-4'); 4.25 (d, J$_{6'a-6'b}$=12.6 Hz, 1H, H-6'a); 4.12 (dd, J$_{6b-6a}$=12.0 e J$_{6b-5}$=4.5 Hz, 1H, H-6b), 4.00 (dd, J$_{6'b-6'a}$=12.6 Hz e J$_{6'b-5'}$=1.5 Hz, 1H, H-6'b); 3.87-3.69 (m, 2H, H4+H5); 3.79 (s, 3H, OMe); 3.42 (pseudo s, 1H, H-5'); 2.09, 2.07, 2.03, 2.02, 2.00 (6×COCH$_3$).

$^{13}$C NMR (CDCl$_3$, 75 MHz): δ ppm 170.8, 170.4, 170.1, 169.6, 168.93, 168.89 (6×COCH$_3$); 160.3, 130.1, 127.9, 113.7 (Ph); 101.3 (CHPh); 101.1 (C-1'); 91.8 (C-1); 75.5, 73.8, 73.2, 72.4, 72.1, 70.5, 69.0, 68.4 (C-2, C-3, C-4, C-5, C-2', C-3', C-4', C-5'); 66.5 (C-6'); 61.6 (C-6), 55.4 (OMe); 20.9-20.6 (6×COCH$_3$).

Rf (AcOEt:hexan=1:1, UV-vis and H$_2$SO$_2$/MeOH)=0.2

Example 5

Preparation of 1,2,3,6,2',3'-hexa-O-acetyl-β-D-lactose

The syrup containing 100 g (0.15 moles) of 1,2,3,6,2',3'-hexa-O-acetyl-4',6'-O-benzylidenlactose obtained according to example 2 was dissolved in 400 ml of glacial acetic acid. The reaction mixture was heated at 80° C. and then 100 ml of water (preheated at 80° C.) were added, stirring the mixture at this temperature for 1.5 hours. The reaction mixture was then rapidly cooled to room temperature and 500 ml of toluene and 350 ml of water were added and extracted. The aqueous layer was extracted with 150 ml of toluene. The combined toluene layer contained not reacted 1,2,3,6,2',3'-hexa-O-acetyl-4',6'-O-benzylidenlactose, which can be used in another reaction. The aqueous layer, containing 1,2,3,6,2',3'-hexa-O-acetyl-β-D-lactose, was extracted successively with 500 ml and 150 ml of methylene chloride; the organic extracts were washed with 3×150 ml of water, dried over anhydrous sodium sulphate and concentrated. The residue was crystallized from 580 ml of hot isopropyl acetate (50-55° C.), obtaining after drying 30.8 g of 1,2,3,6,2',3'-hexa-O-acetyl-β-D-lactose (0.05 mol) as a chalky white solid. Considering that in the combined toluene layers 20.2 g of unreacted 1,2,3,6,2',3'-hexa-O-acetyl-4',6'-O-benzylidenlactose (0.03 mol) were recovered, the yield is 42%.

Mp 188-190° C.

$^1$H NMR (CDCl$_3$, 300 MHz): δ ppm 5.68 (d, J$_{1-2}$=8.1 Hz, 1H, H-1), 5.24 (pseudo t, J$_{3-2}$=J$_{3-4}$=9.3 Hz, 1H, H-3), 5.19 (dd, J$_{2'-3'}$=10.2 Hz e J$_{2'-1'}$=7.8 Hz, 1H, H-2'), 5.05 (dd, J$_{2-3}$=9.3 Hz e J$_{2-1}$=8.1 Hz, 1H, H-2), 4.88 (dd, J$_{3'-2'}$=10.2 Hz e J$_{3'-4'}$=3.3 Hz, 1H, H-3'), 4.49 (d, J$_{1'-2'}$=7.8 Hz, 1H, H-1'), 4.49 (dd, J$_{6a-6b}$=11.1 Hz e J$_{6a-5}$=1.8 Hz, 1H, H-6a), 4.15-4.05 (m, 2H, H-4'+H-6b), 4.00-3.70 (m, 4H, H-4+H-5+H-6'a+H-6'b), 3.56 (pseudo t, J=5.4 Hz, 1H, H-5'), 2.96 (d, J$_{OH-4'}$=4.2 Hz, C4'-OH), 2.59 (dd, J$_{OH-6}$=7.5 e 4.8 Hz, C6'-OH), 2.11, 2.09, 2.08, 2.07 2.04, 2.03 (6×COCH$_3$).

$^{13}$C NMR (CDCl$_3$, 75 MHz): δ ppm 170.6, 170.4, 170.3, 169.7, 169.6, 169.0 (6×COCH$_3$); 101.2 (C-1'), 91.7 (C-1), 75.9 (C-4), 74.6 (C-5'), 73.7 (C-3'), 73.6 (C-5), 73.1 (C-3), 70.7 (C-2), 69.7 (C-2'), 67.8 (C-4'), 62.1, 62.0 (C-6, C-6'), 20.9, 20.8, 20.7 (6×COCH$_3$).

Rf (AcOEt, UV-vis and H$_2$SO$_4$/MeOH)=0.4

Example 6

Preparation of di 1,2,3,6,2',3'-hexa-O-acetyl-β-D-lactose

The syrup containing 100 g (0.14 mol) of 1,2,3,6,2',3'-hexa-O-acetyl-4',6'-O-p-methoxybenzylidenlactose obtained according to example 4 was dissolved in 400 ml of glacial acetic acid, then 100 ml of water were added and the mixture was stirred at room temperature for 4.5 hours. 500 ml of toluene and 350 ml of water were added then extracted. The aqueous layer was extracted with 150 ml of toluene. The collected toluene layer contained 1,2,3,6,2',3'-hexa-O-acetyl-4',6'-O-p-methoxybenzylidenlactose not reacted, which can be used in another reaction. The aqueous layer, containing 1,2,3,6,2',3'-hexa-O-acetyl-β-D-lactose, was extracted successively with 500 ml and 150 ml of methylene chloride; the organic extracts were washed with 3×150 ml of water, dried on anhydrous sodium sulphate and concentrated. The residue was crystallized from 580 ml of hot isopropyl acetate (50-55° C.) obtaining, after drying, 40.6 g of 1,2,3,6,2',3'-hexa-O-acetyl-β-D-lactose (0.07 mol, yield 50%) as white powdery solid whose characteristics are similar to the solid obtained from Example 5.

Example 7

Preparation of (methyl 5-acetamido-4,7,8,9-tetra-O-acetyl-3,5-dideoxy-D-glycero-α-D-galacto-non-2-ulopyranosylonate)-(2→6)-2,3-di-O-acetyl-β-D-galactopyranosyl-(1→4)-1,2,3,6-tetra-O-acetyl-β-D-glucopyranose 100 g (0.168 mol) of 1,2,3,6,2',3'-hexa-O-acetyl-β-D-lactose, obtained according to example 3, were dissolved in 600 ml of dichloromethane, then 250 g of molecular sieves 3A were added. The solution was stirred for 5-10 min and then 38.0 g of silver carbonate (0.14 mol) were added. A solution of 128.5 g (0.252 mol) (1.5 eq) of chlorine derivative of formula (II) wherein P is acetyl, X is chloro and R1 is methyl, in 500 ml of dichloromethane was added and the suspension was maintained in vigorous stirring at 30° C. for 7 days until chlorine derivative disappeared (TLC, CH$_2$Cl$_2$:MeOH=10: 1), then the reaction mixture was filtered on dicalite and the solvent removed, obtaining a brittle solid residue (about 230 g), containing a mixture of condensation product, 1,2,3,6,2', 3'-hexa-O-acetyl-β-D-lactose and product of 2.3 elimination of (II), as well as a trace of 4,7,8,9-tetra-O-acetyl-NANA. By $^{13}$C NMR a conversion of about 90% mol was evaluated. An analytical sample of the condensate product was obtained by crystallization from ethanol:isopropyl ether=1:3 v/v as a white amorphous solid:

$^1$H NMR (CDCl$_3$, 300 MHz): δ ppm 5.66 (d, J$_{1-2}$=8.4 Hz, 1H, H-1); 5.42-5.10 (m, 5H, H-3+H-2'+H-7"+H-8"+NH); 5.01 (pseudo t, J$_{2-1}$=8.4 Hz, 1H, H-2); 4.94-4.78 (m, 2H, H-3'+H-4"); 4.53-4.27 (m, 3H, H-1'+H-6a+H-9"); 4.24-3.92 (m, 5H, H-6b+H-4'+H-5"+H-6"+H-9"b); 3.92-3.50 (m, 5H, H-4+H-5+H-5'+H-6'a+H-6'b); 3.80 (s, 3H, COOCH$_3$), 2.93

(broad s, 1H, OH); 2.55 (dd, $J_{3''eq-3''ax}$=12.6 e $J_{3''eq-4''}$=4.5 Hz, 1H, H-3"eq); 2.17-1.97 (31H, 10×CH$_3$CO e H-3"ax), 1.86 (s, 3H, NHCOCH$_3$).

$^{13}$C NMR (CDCl$_3$: 75 MHz): δ ppm 171.05, 170.98, 170.5, 170.4, 170.29, 170.28, 170.24, 170.0, 169.6, 169.4, 169.0, 168.0 (OAc, NHAc, COOMe); 100.8 (C-1'); 99.1 (C-2"); 91.7 (C-1); 75.7, 73.7, 73.6, 72.94, 72.90, 72.4, 70.7, 69.7, 68.95, 68.87, 67.4, 66.3 (C-2, C-3, C-4, C-5, C-2', C-3', C-4', C-5', C-4", C-6", C-7", C-8"); 62.6, 62.4, 62.1 (C-6, C-6', C-9"); 53.2 (OCH$_3$); 49.4 (C-5"); 37.4 (C-3"); 23.2 (NHCOCH$_3$), 21.1, 20.9, 20.8, 20.74, 20.67 (10×CH$_3$CO).

Example 8

Preparation of (methyl 5-acetamido-3,5-dideoxy-D-glycero-α-D-galacto-non-2-ulopyranosylonate)-(2→6)-β-D-galactopyranosyl-(1→4)-(α/β)-D-glucopyranose 230 g of the crude product, obtained according to example 7, were dissolved in 1.4 l of MeOH, then 29.6 ml of sodium methoxide in methanol 25% by weight was added. The solution was kept stirring at room temperature for 12 h; at positive TLC control (Pharmacopoeia) it was neutralized with 39 g of dry IR120 (H$^+$). The resin was filtered and the solvent removed by rotavapor, obtaining 143 g of residue, used in next reaction. The yield was quantitative.

$^1$H NMR (D$_2$O, 300 MHz): δ ppm 5.21 (d, $J_{1-2}$ 3.6 Hz, 1H, H-1α), 4.66 (d, $J_{1-2}$ 7.8 Hz, 1H, H1β), 4.42 (d, $J_{1'-2'}$: 7.5 Hz, 1H, H-1'), 4.15-3.45 (m, 19H), 3.89 (s, 3H, COOCH$_3$), 3.29 (m, 1H), 2.70 (dd, $J_{3''eq-3''ax}$ 12.9 e $J_{3''eq-4''}$ 4.8 Hz, H-3"eq), 2.03 (s, 3H, NHCOCH$_3$), 1.88 (pseudo t, $J_{3''ax-3''eq}$=$J_{3''ax-4''}$ 12.9 Hz, H-3"ax).

$^{13}$C NMR (D$_2$O, 75 MHz): δ ppm 175.5 (NHCOCH$_3$), 170.4 (COOMe), 103.9 (C-1'), 99.6 (C-2"), 96.3 (C-1β), 92.5 (C-1α), 80.5, 80.4, 75.2 (2C), 74.4, 74.0, 73.5, 73.0, 72.2, 71.7, 71.3, 71.2, 70.5, 69.0 (2C), 67.9 (C-2, C-3, C-4, C-5, C-2', C-3', C-4', C-5', C-4", C-6", C-7", C-8"), 64.0 (C-6'), 63.8 (C-9"), 60.8 e 60.7 (C-6α+β), 54.1 (COOCH$_3$), 52.3 (C-5"), 39.6 (C-3"), 22.8 (NHCOCH$_3$).

Example 9

Preparation of sodium 5-acetamido-3,5-dideoxy-D-glycero-α-D-galacto-non-2-ulopyranosylonate-(2→6)-β-D-galactopyranosyl-(1→4)-(α/β)-D-glucopyranose 143 g of the crude deacetylation product, obtained according to example 8, were dissolved in 715 ml of water and the solution was cooled at 4° C. The pH was brought to neutrality with aqueous NaOH and then 23 ml of NaOH 30% were added, maintaining the temperature of the solution below 10° C. The solution was stirred at room temperature for 24 h. At positive TLC control (Pharmacopoeia) the solution was passed through IR120(H$^+$)/IRA96(OH$^-$). The eluate was adjusted to pH 9 with NaOH, concentrated to syrup, and submitted to stripping several times with absolute EtOH until obtaining a brittle white solid that is re-crystallized from EtOH 96%. Obtained 77.3 gr.

$^1$H and $^{13}$C NMR data for this compound were in agreement with those reported in the literature (L. Dorland et al., *Eur. J. Biochem.* 1978, 87, 323; J. P. Kamerling et al., *Carbohydr. Res.* 1982, 100, 331).

$^1$H NMR (D$_2$O, 300 MHz): δ ppm 5.22 (d, $J_{1-2}$ 3.8 Hz, 1H, H-1α), 4.66 (d, $J_{1-2}$ 7.8 Hz, 1H, H-1β), 4.43 (d, $J_{1'-2'}$: 7.6 Hz, 1H, H-1'), 4.02-3.48 (m, 19H), 3.31 (m, 1H), 2.71 (dd, $J_{3''eq-3''ax}$ 12.5 e $J_{3''eq-4''}$ 4.7 Hz, H-3"eq), 2.03 (s, 3H, NHCOCH$_3$), 1.74 (pseudo t, $J_{3''ax-3''eq}$=$J_{3''ax-4''}$ 12.5 Hz, H-3"ax).

$^{13}$C NMR (D$_2$O, 75 MHz, external reference acetone): δ ppm 175.6 (NHCOCH$_3$), 174.1 (COO$^-$), 103.9 (C-1'), 100.9 (C-2"), 96.3 (C-1β), 92.5 (C-1α), 80.4, 80.3, 75.30, 75.26, 74.4, 74.3, 73.2, 73.0, 72.4, 72.3, 71.7, 71.4, 70.6, 69.2, 69.04, 69.01 (C-2, C-3, C-4, C-5, C-2', C-3', C-4', C-5', C-4", C-6", C-7", C-8"), 64.2 (C-6'), 63.3 (C-9"), 60.9 e 60.8 (C-6α+β), 52.4 (C-5"), 40.7 (C-3"), 22.7 (NHCOCH$_3$).

$[α]_D^{20° C.}$: +9.3° (c: 1%, H$_2$O)

Mp: 191.4÷194.2° C. (T decomposition)

Example 10

Preparation calcium 5-acetamido-3,5-dideoxy-D-glycero-α-D-galacto-non-2-ulopyranosylonate-(2→6)-β-D-galactopyranosyl-(1→4)-(α/β)-D-glucopyranose 100 g of crude deacetylation, obtained according to example 8, were dissolved in 500 ml of water and the solution was cooled at 4° C. The pH was brought to neutrality with aqueous NaOH and then 23 ml of NaOH 30% were added, maintaining the temperature of the solution below 10° C. The resulting solution was kept stirring at room temperature for 24 h. At positive TLC control (Pharmacopoeia) the solution was passed through IR120 (H$^+$)/IRA96(OH$^-$). The eluate was adjusted at pH 8.7 with Ca(OH)$_2$, filtered and then concentrated to syrup at 65° Brix. This syrup was dropped in 540 ml of methanol at 50° C. The resulting suspension was maintained in vigorous stirring at 50° C. for 1 hour, then at room temperature for 1 hour and then filtered under vacuum. The solid was washed with 160 ml of methanol and dried under vacuum at 50÷55° C. Obtained: 46.2 g $^1$H NMR (D$_2$O, 300 MHz): δ ppm 5.22 (d, $J_{1-2}$ 3.8 Hz, 1H, H-1α), 4.66 (d, $J_{1-2}$ 7.8 Hz, 1H, H-1β), 4.43 (d, $J_{1'-2'}$: 7.8 Hz, 1H, H-1'), 4.02-3.48 (m, 19H), 3.31 (m, 1H), 2.71 (dd, $J_{3''eq-3''ax}$ 12.0 e $J_{3''eq-4''}$ 4.5 Hz, H-3"eq), 2.03 (s, 3H, NHCOCH$_3$), 1.74 (pseudo t, $J_{3''ax-3''eq}$=$J_{3''ax-4''}$ 12.0 Hz, H-3"ax).

$^{13}$C NMR (D$_2$O, 75 MHz, internal reference acetonitrile): δ ppm 175.5 (NHCOCH$_3$), 174.1 (COO$^-$), 103.8 (C-1'), 100.9 (C-2"), 96.2 (C-1β), 92.4 (C-1α), 80.3, 80.3, 75.26, 75.22, 74.4, 74.3, 73.1, 73.0, 72.4, 72.2, 71.7, 71.4, 70.5, 69.1, 69.13, 69.00 (C-2, C-3, C-4, C-5, C-2', C-3', C-4', C-5', C-4", C-6", C-7", C-8"), 64.2 (C-6'), 63.2 (C-9"), 60.9 e 60.7 (C-6α+β), 52.4 (C-5"), 40.7 (C-3"), 22.7 (NHCOCH$_3$).

Assay as Ca$^{2+}$: 98.3%

$[α]_D^{20° C.}$: +10° (c: 1%, H$_2$O)

Mp: 204.5÷206.6° C. (T decomposition)

IR ν$^{KBr}_{max}$: 3400, 1612, 1380, 1033 cm$^{-1}$.

Example 11

Preparation of potassium 5-acetamido-3,5-dideoxy-D-glycero-α-D-galacto-non-2-ulopyranosylonate-(2→6)-β-D-galactopyranosyl-(1→4)-(α/β)-D-glucopyranose 100 g of the crude deacetylation product, obtained according to example 8, were dissolved in 500 ml of water and the solution was cooled at 4° C. The pH was brought to neutrality with aqueous NaOH and then 23 ml of NaOH 30% were added, maintaining the temperature of the solution below 10° C. The solution was stirred at room temperature for 24 h. At positive TLC control (Pharmacopoeia) the solution was passed through IR120(H$^+$)/IRA96(OH$^-$). The eluate was adjusted to pH 10 with KOH, concentrated to syrup, and submitted to stripping several times with absolute EtOH until obtaining a white brittle solid that is re-crystallized from absolute EtOH. The solid was dried under vacuum at 50÷55° C.

Obtained 35.7 gr $^1$H NMR (D$_2$O, 200 MHz): δ ppm 5.22 (d, J$_{1-2}$ 3.8 Hz, 1H, H-1α), 4.66 (d, J$_{1-2}$ 7.8 Hz, 1H, H-1β), 4.43 (d, J$_{1'-2'}$: 7.6 Hz, 1H, H-1'), 4.02-3.48 (m, 19H), 3.31 (m, 1H), 2.71 (dd, J$_{3''eq-3''ax}$ 12.0 e J$_{3''eq-4''}$ 4.4 Hz, H-3''eq), 2.03 (s, 3H, NHCOCH$_3$), 1.74 (pseudo t, J$_{3''ax-3''eq}$=J$_{3''ax-4''}$ 12.0 Hz, H-3''ax).

$^{13}$C NMR (D$_2$O, 75 MHz, internal reference acetone): δ ppm 175.5 (NHCOCH$_3$), 174.0 (COO$^-$), 103.8 (C-1), 100.9 (C-2''), 96.2 (C-1β), 92.4 (C-1α), 80.3, 80.2, 75.22, 75.19, 74.4, 74.3, 73.1, 72.9, 72.4, 72.2, 71.7, 71.4, 70.5, 69.1, 69.04, 69.01 (C-2, C-3, C-4, C-5, C-2', C-3', C-4', C-5', C-4'', C-6'', C-7'', C-8''), 64.1 (C-6'), 63.2 (C-9''), 60.8 e 60.7 (C-6α+β), 52.4 (C-5''), 40.7 (C-3''), 22.6 (NHCOCH$_3$).

$[α]_D^{20°\,C}$: +9.8° (c: 1%, H$_2$O)

Mp: 179.3÷182.8° C. (T decomposition)

IR $ν^{KBr}_{max}$: 3391, 1612, 1379, 1034 cm$^{-1}$.

Example 12

Preparation of magnesium 5-acetamide-3,5-dideoxy-D-glycero-α-D-galacto-non-2-ulopyranosylonate-(2→6)-β-D-galactopyranosyl-(1→4)-(α/β)-D-glucopyranose 100 g of the crude deacetylation product, obtained according to example 8, were dissolved in 500 ml of water and the solution was cooled at 4° C. The pH was brought to neutrality with aqueous NaOH and then 23 ml of NaOH 30% were added, maintaining the temperature of the solution below 10° C. The solution was stirred at room temperature for 24 h. At positive TLC control (Pharmacopoeia) the solution was passed through IR120(H$^+$)/IRA96(OH$^-$). The eluate was adjusted to pH 9.8 with MgO, concentrated to residue submitted to stripping several times with absolute EtOH until obtaining a white friable solid that is re-crystallized from absolute EtOH.

Obtained: 50.8 g $^1$H NMR (D$_2$O, 300 MHz): δ ppm 5.22 (d, J$_{1-2}$ 3.6 Hz, 1H, H-1α), 4.66 (d, J$_{1-2}$ 8.1 Hz, 1H, H-1β), 4.43 (d, J$_{1'-2'}$: 7.5 Hz, 1H, H-1'), 4.02-3.48 (m, 19H), 3.31 (m, 1H), 2.71 (dd, J$_{3''eq-3''ax}$ 12.3 e J$_{3''eq-4''}$ 4.5 Hz, H-3''eq), 2.03 (s, 3H, NHCOCH$_3$), 1.74 (pseudo t, J$_{3''ax-3''eq}$=J$_{3''ax-4''}$ 12.3 Hz, H-3''ax).

$^{13}$C NMR (D$_2$O, 75 MHz, internal reference acetonitrile): δ ppm 175.5 (NHCOCH$_3$), 174.1 (COO$^-$), 103.8 (C-1'), 100.9 (C-2''), 96.3 (C-1β), 92.4 (C-1α), 80.3, 80.2, 75.26, 75.23, 74.4, 74.3, 73.1, 73.0, 72.4, 72.2, 71.7, 71.4, 70.6, 69.1, 69.00, 68.96 (C-2, C-3, C-4, C-5, C-2', C-3', C-4', C-5', C-4'', C-6'', C-7'', C-8''), 64.2 (C-6'), 63.3 (C-9''), 60.9 e 60.7 (C-6α+β), 52.4 (C-5''), 40.7 (C-3''), 22.7 (NHCOCH$_3$).

Assay as Mg$^{2+}$: 97.5%

$[α]_D^{20°\,C}$: +9.8° (c: 1%, H$_2$O)

Mp: 183.1÷185.1° C. (T decomposition)

IR $ν^{KBr}_{max}$: 3391, 1634, 1379, 1035 cm$^{-1}$.

The invention claimed is:

1. A Compound of formula (Ib)

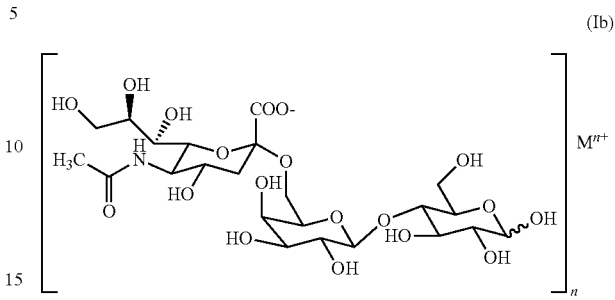

(Ib)

wherein $M^{n+}$ is chosen from the group consisting of Ca$^{2+}$, Mg$^{2+}$, Sr$^{2+}$, Fe$^{2+}$ and Al$^{3+}$.

2. The compound according to claim 1 wherein $M^{n+}$ is chosen from the group consisting Ca$^{2+}$ and Mg$^{2+}$.

3. The compound according to claim 1 wherein $M^{n+}$ is Ca$^{2+}$.

4. A process for preparation of the compound according to claim 1, starting from 6'-sialyllactose (6'SL), said process comprising adding a base containing $M^{(n+)}$ to a solution of 6'SL to obtain a pH value of 8-10 of the solution.

5. A process for preparation of the compound of claim 1 said process comprising at least a step of:

a) Coupling, a sialyc donor of formula (II)

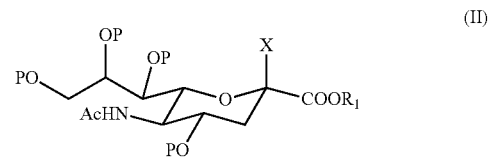

(II)

in which P is a suitable-protecting group; R$_1$ is alkyl, and X is halogen;

with an acceptor of formula R'OH, in which R' is a residue lactose suitably-protected with protecting groups P' and containing zero, one or more free hydroxy groups; and in which said protecting groups P' can be the same or different among each other and from those present in the donor;

to obtain an intermediate of formula (III)

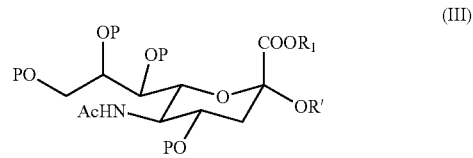

(III)

in which P, R1 and R' are as defined above, wherein the coupling is performed by a Koenigs-Knorr reaction involving a Ag(I) based metallic promoter in molar amounts of 0.5-2.0 equivalents with respect to moles of the acceptor;

b) removing P, P' and $R_1$ to obtain the compound of formula (Ia)

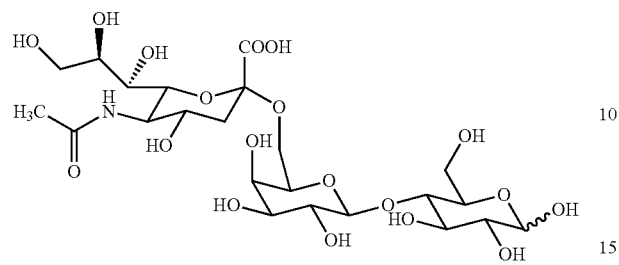

(Ia)

c) adding a base containing the $M^{(n+)}$ to a solution of the compound of formula (Ia) to obtain the compound of formula (1b).

6. A medicament or food integrator comprising the compound according to claim 1.

7. A pharmaceutical or food composition comprising the compound of claim 1 and at least one other ingredient, pharmaceutically or alimentary acceptable.

* * * * *